United States Patent [19]

Durand

[11] Patent Number: 5,405,329
[45] Date of Patent: Apr. 11, 1995

[54] INTRAVASCULAR MULTI-LUMEN CATHETER, CAPABLE OF BEING IMPLANTED BY "TUNNELLING"

[76] Inventor: Alain J. Durand, 14, rue du Grand Couvent, F-3000 Nimes, France

[21] Appl. No.: 815,191

[22] Filed: Dec. 31, 1991

[30] Foreign Application Priority Data

Jan. 8, 1991 [FR] France .................. 91 00139

[51] Int. Cl.⁶ .............................. A61M 5/178
[52] U.S. Cl. ..................... 604/164; 604/43; 604/280; 604/96
[58] Field of Search ......... 604/43, 244, 247, 280, 604/283, 264, 96, 164

[56] References Cited

U.S. PATENT DOCUMENTS

| | | | |
|---|---|---|---|
| 4,453,928 | 6/1984 | Steiger . | |
| 4,583,968 | 4/1986 | Mahurkar | 604/43 |
| 4,619,641 | 10/1986 | Schanzer | 604/244 X |
| 4,619,643 | 10/1986 | Bai . | |
| 4,626,240 | 12/1986 | Edelman et al. | 604/43 |
| 4,666,426 | 5/1987 | Aigner | 604/43 X |
| 4,682,978 | 7/1987 | Martin | 604/43 |
| 4,692,141 | 9/1987 | Mahurkar | 604/43 |
| 4,950,259 | 8/1990 | Geary et al. | 604/43 X |
| 5,057,073 | 10/1991 | Martin | 604/43 |
| 5,106,368 | 4/1992 | Uldall et al. | 604/43 |
| 5,135,559 | 8/1992 | Martin et al. | 604/43 X |
| 5,188,593 | 2/1993 | Martin | 604/43 |

FOREIGN PATENT DOCUMENTS 0263645 4/1988 European Pat. Off. .

*Primary Examiner*—Randall L. Green
*Assistant Examiner*—Rob Clarke
*Attorney, Agent, or Firm*—Young & Thompson

[57] ABSTRACT

This intravascular catheter comprises a multi-aperture pipe design for the perfusion of medicines which are mutually incompatible in their pure state or for carrying out several different functions. In order to permit the implantation of this catheter by the "tunnelling" method, this multi-aperture pipe (1) forms only the distal part of this catheter. The catheter also comprises separate tubes (2a, 2b) equal in number to the apertures of the first pipe and which extend back from this pipe to form the middle part (2) of the catheter; and a single-aperture pipe (3) forming the proximal end of the assembly which terminates in a rigid needle (4) suitable for carrying out the tunnelling. Two connectors (5 and 6) serve respectively to join each aperture (1a, 1b) of the multi-aperture pipe (1) to one of the separate tubes (2a or 2b) of the middle part (2), and to connect the opposite ends of these tubes (2a, 2b) to the corresponding end of the single-aperture pipe (3). Each of these connectors is made of plastic and is molded onto the ends of the parts to be joined.

3 Claims, 5 Drawing Sheets

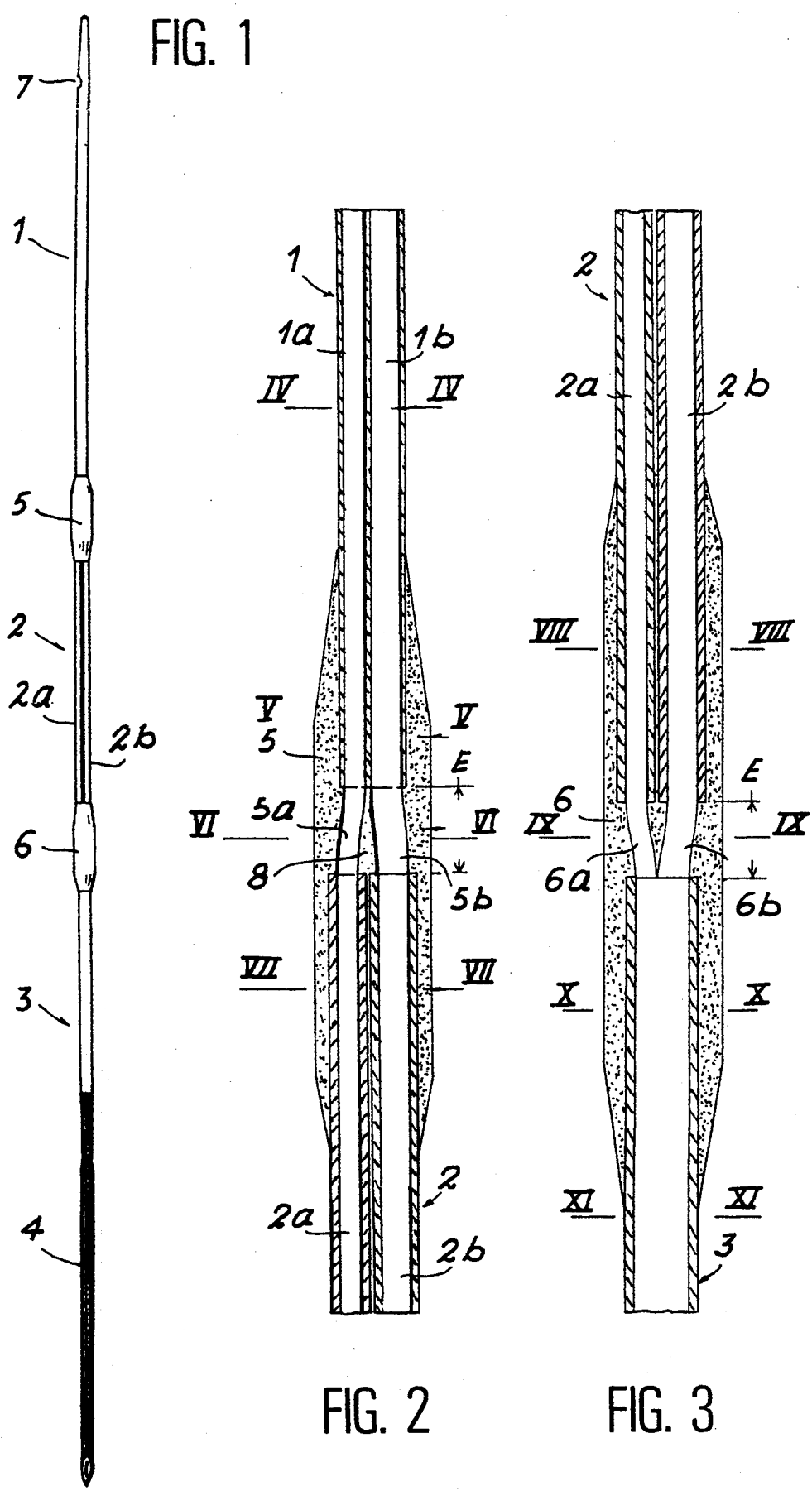

INTRAVASCULAR MULTI-LUMEN CATHETER, CAPABLE OF BEING IMPLANTED BY "TUNNELLING"

The present invention concerns a medical instrument of the catheter type the pipe of which comprises at least two apertures.

The term "medical" is used here in the broadest sense and concerns veterinary applications as well as those relating to human medicine, while the designation "intravascular catheter" applies to a device which must be placed in the patient's vascular system, by puncturing the selected vessel.

When a catheter is intended for prolonged use on a patient, the catheter is placed in position by means of the SELDINGER technique, which consists of puncturing a vessel with a fine needle, the aperture of which allows the passage of a fine spiral guide, withdrawing the needle when the guide has been inserted sufficiently far into the vessel, then advancing the catheter pipe along the guide and finally withdrawing the guide, leaving the catheter in place in the vessel. However in general the catheter pipe is also "tunnelled" over a certain length. This process consists of causing the catheter pipe to follow a course of several centimeters between the point at which the vessel is punctured and the external surface of the patient's body, more or less parallel to the skin and some millimeters from the surface. Thus all external germs liable to pass along the catheter pipe to the punctured vessel, or to one of the patient's organs, come up against the natural obstacle formed by the tissues crossed when the "tunnelling" is carried out.

A catheter specially designed for the application of this technique is described in U.S. Pat. No. 2,522,504. However this relates to a single-aperture catheter.

The development of diagnostic and therapeutic techniques has shown the need for catheters composed of a multi-aperture pipe, so that several separate apertures can be used, either for identical but nevertheless necessarily independent functions, for example, in the case of the simultaneous perfusion of two medicines which are mutually incompatible in their pure state, or for different functions, for example, monitoring intravascular pressure or the concentration of $CO_2$ perfusion, taking blood samples etc.

With existing equipment, it is very difficult for a practitioner to apply the practice of "tunnelling" to a catheter with several apertures which inevitably has a larger cross-section than a catheter with a single aperture. Furthermore, it is then necessary to open up in the patient's flesh a passage with a diameter considerably greater than the external diameter of the catheter, which has the effect of cancelling out, or at the very least reducing, the role of the barrier to external attack, which is precisely what the practice of tunnelling seeks to achieve.

For this reason the aim of the present invention is to produce a catheter device with several apertures which can nevertheless be inserted by tunnelling without encountering the disadvantages explained above.

To this end the multi-aperture pipe of this catheter constitutes only the distal part of the catheter which also comprises:

separate tubes equal in number to the apertures of the first pipe, which extend back from the latter to form the middle part of the catheter, a pipe with a single aperture forming the proximal end of the assembly, which terminates in a rigid needle suitable for use in tunnelling, two connectors which respectively join each aperture of the multi-aperture pipe to one of the separate tubes of the middle part and connect the opposite ends of these tubes to the corresponding end of the single-aperture pipe, each of these connectors being made up of a body in the shape of a tapered olive, made of plastic and moulded onto the ends of the parts to be joined.

Thanks to the subdivision of this catheter into several parts which are distinct in character and the joining of these latter by means of moulded-on tapered connectors, the technique of tunnelling can be practised without difficulty. After the application of this technique, only the distal multi-aperture pipe remains implanted in the patient's body, so that the catheter only has to be cut in the middle part to make available two or more independent tubes to which detachable connectors can simply be connected as required.

However the present invention also concerns a specific process for manufacturing a catheter device such as that defined above. Moreover, other distinctive features and advantages of the subject of the invention will appear in the course of the description that follows. The description is given in reference to the drawing which is attached for information only, and in which:

FIG. 1 is a plan view from above of a catheter according to the invention.

FIG. 2 is a partial view in longitudinal section, of the upper of the two connectors on the catheter shown in FIG. 1.

FIG. 3 is a partial view in longitudinal section, of the lower of the two connectors on the catheter shown in FIG. 1.

Figure 4:
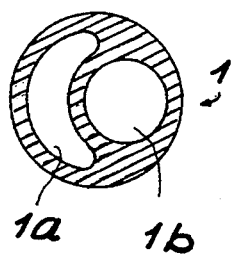
FIG. 4 is a view in transverse section along line IV—IV of FIG. 2, but on a different scale.
Figure 8:
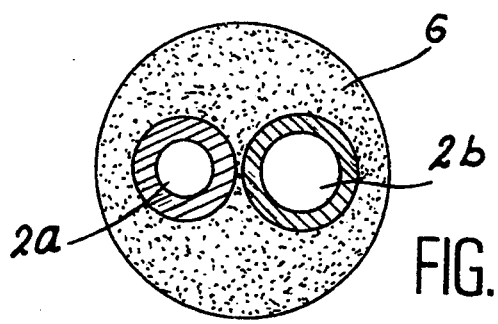
FIG. 8 is a view in transverse section along line VIII—VIII of FIG. 3, but on a different scale.
Figure 5:
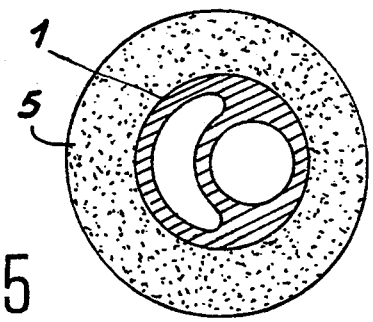
FIG. 5 is a view in transverse section along line V—V of FIG. 2, but on a different scale.
Figure 9:
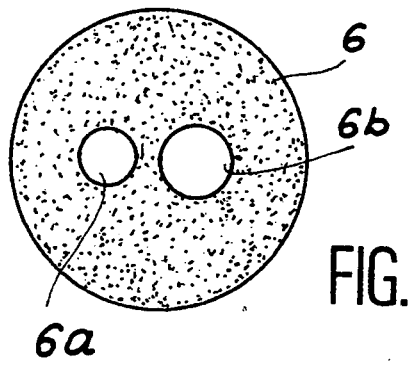
FIG. 9 is a view in transverse section along line IX—IX of FIG. 3, but on a different scale.
Figure 6:
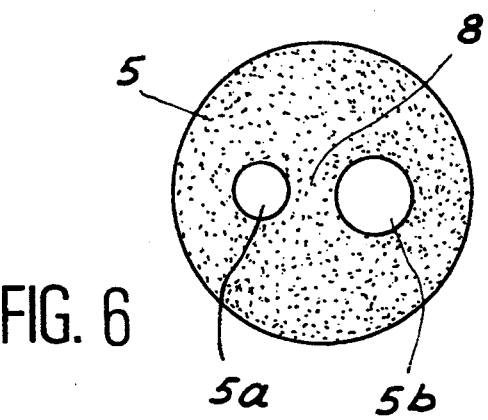
FIG. 6 is a view in transverse section along line VI—VI of FIG. 2, but on a different scale.
Figure 10:
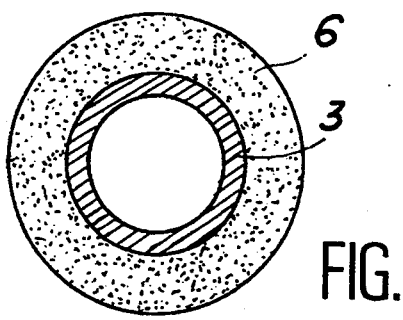
FIG. 10 is a view in transverse section along line X—X of FIG. 3, but on a different scale.
Figure 7:
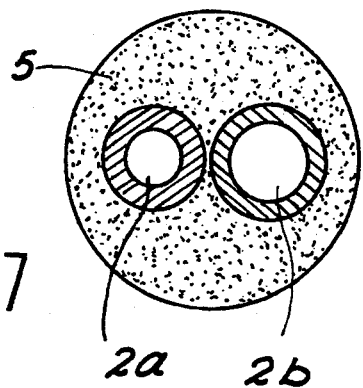
FIG. 7 is a view in transverse section along line VII—VII of FIG. 2, but on a different scale.
Figure 11:
FIG. 11 is a view in transverse section along line XI—XI of FIG. 3, but on a different scale.

As has already been indicated, the catheter illustrated in FIGS. 1 to 12 comprises three successive parts with different structures, namely:

a distal part designated by the general reference 1 which is made up of a multi-aperture pipe, in this case, in the example illustrated, a pipe comprising two apertures 1a and 1b, a middle part designated by the general reference 2 which is made up of separate tubes 2a and 2b, equal in number to the apertures 1a and 1b of the distal part, a proximal part designated by the general reference 3 which is made up of a single-aperture pipe terminating in a rigid needle 4 suitable for tunnelling.

As for the free end of the distal part 1, a special feature of this is that only one of the apertures of pipe 1 opens out at this point, so that it can be used for sliding the assembly along the spiral guide used to position the catheter. The other aperture of the distal part 1 opens through a small orifice 7 provided on the side, close to the end.

These three successive parts 1, 2 and 3 are joined by means of two connectors 5 and 6 which are each made up of a plastic body in the shape of a tapered olive, moulded onto the ends of the parts to be joined.

FIG. 2 and FIGS. 4 to 7 illustrate the first connector 3 which joins the distal part 1 to the middle part 2.

Apart from the distinctive external shape of this connector, another of its essential characteristics resides in the fact that there is a space E between the ends of the pipes connected by this connector. The corresponding part of the body of the connector comprises two channels 5a and 5b formed on the inside of the moulded material with a space between them in the transverse direction (see FIG. 6). Also there is to some extent a connecting bridge 8 between the moulded-on parts on either side of the plane passing through the axes of channels 5a and 5b. This ensures that the body of the connector 5 and the corresponding pipes are firmly joined to make a whole, by preventing in particular any possibility of sliding in the longitudinal direction.

Figure 12:
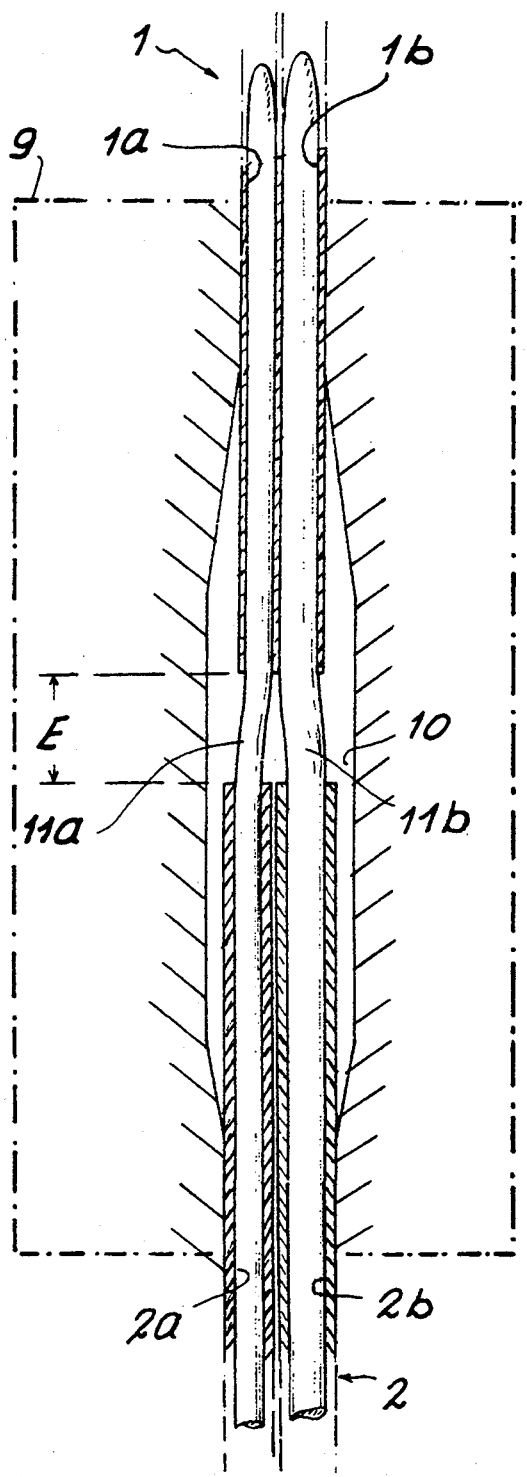
FIG. 12 is a diagrammatic sectional view of the mould used to make the connector illustrated in FIG. 2.
Figure 13:
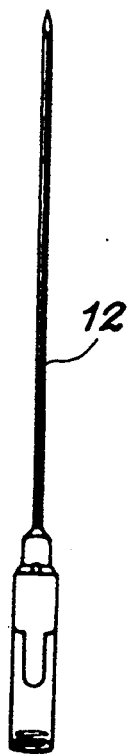
FIG. 13 is a plan view of the puncture needle used to position the present catheter.
Figure 21:
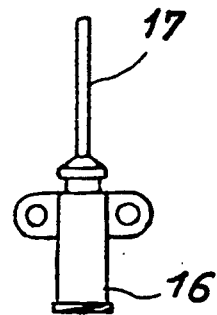
FIG. 21 is a plan view from above of one of the detachable connectors which are later connected to one of the tubes of the middle part of the catheter after tunnelling.
Figure 14:
FIG. 14 is a diagram of the first stage of the tunnelling operation.
Figure 15:
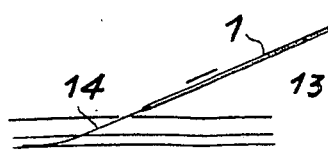
FIG. 15 is a diagram of the second stage of the tunnelling operation.
Figure 16:
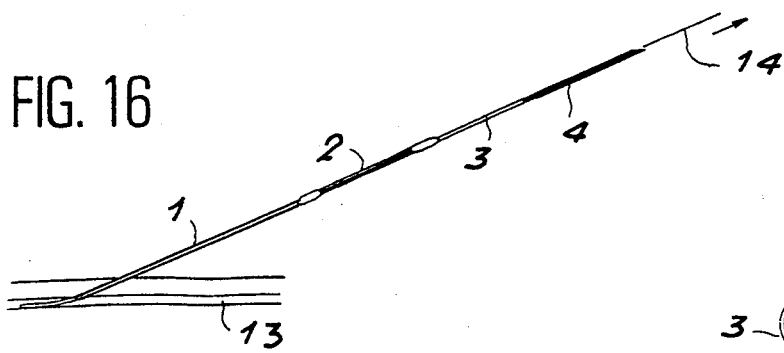
FIG. 16 is a diagram of the third stage of the tunnelling operation.

FIG. 12 shows the mould used to make this connector. Before the ends of the pipes 1 and 2 are positioned inside the moulding cavity 10 of this mould, two mandrels 11a and 11b are inserted into these pipes. In this instance the first mandrel 11a is inserted into both the aperture 1a of pipe 1 and one of the tubes 2a of the middle part 2 of the catheter. The other mandrel is, of course, inserted into both the aperture 1b of pipe 1 and tube 2b of the middle part 2. But the space E is then preserved between the corresponding ends of the pipes to be joined. Thus the two mandrels 11a and 11b ensure the formation of the connecting channels 5a and 5b inside the corresponding part of the body of the connector 5.

It should be noted that in this embodiment the connector forms a sleeve round both the corresponding end of the pipe 1 with two apertures and the neighbouring ends of the two tubes 2a and 2b of the middle part of the catheter. However the thickness of the walls of this sleeve is reduced to the minimum technically possible, so that the transverse section of the connector 5 is itself reduced to facilitate the subsequent tunnelling of the catheter.

To ensure that the assembly is secure after moulding on, the corresponding part of the catheter is then placed between two welding electrodes of which the active part has the same shape as the mould used for moulding-on. A high-frequency current is then applied which melts, or at least sufficiently softens, the assembly so that it forms one piece. To this end it is advisable to choose plastics from the same family to form the different pieces. For example, if aliphatic polyurethane is chosen to make the pipes, the material used for the moulded-on connectors should also be an aliphatic polyurethane, and the degrees of hardness of these polyurethanes should, if possible, be very close, which also means that their melting points will be similar.

The connector 6 which connects the middle part 2 to the proximal part 4 is made in the same way as connector 5 and with a similar mould. Here too there is a space E between the ends of the pipes to be joined, for the same purpose as before. At this point the body of connector 6 therefore has two channels 6a and 6b which are separated from each other and which each ensure the connection of a tube 2a or 2b with the single aperture of pipe 3.

The diagrams in FIGS. 14 to 20 illustrate the different successive stages of the operation of putting the catheter in place using the tunnelling method:

A—After the usual disinfection procedure, the practitioner punctures the tissue that he has chosen to catheterise using a puncture needle 12 approximately 8 cm long, which enables the selected vessel 13, for example the subclavian vein or the femoral vein, to be reached easily, even on an obese patient. In general, the practitioner does not manipulate this needle directly, but starts by attaching it to a syringe fitted with an ISO standardised tip of the "luer"-type or a "luer" lock. Once a good reflux of blood has been obtained, the practitioner withdraws the syringe and inserts, in the needle 12, a spiral metal guide 14 for a distance of about fifteen centimeters (see FIG. 14).

B—Holding the end of the guide by pressure on the vein beyond the tip of the puncture needle 12, the practitioner withdraws this puncture needle and discards it. With one hand the practitioner then takes hold of the end of the spiral guide 14 remaining outside the patient and fits to it the distal end of the catheter 1-2-3 according to the invention. He then advances the whole of this catheter along the guide 14 until it is able to penetrate the selected vessel 13, still following the course of the guide 14 previously put in place (see FIG. 15).

C—When the catheter has advanced sufficiently far, the spiral guide 14 goes beyond the end of the needle 4. The practitioner can then take hold of this guide and withdraw it gently without changing the position of the end of the catheter which is situated in the vessel 13 (see FIG. 16).

Figure 17:
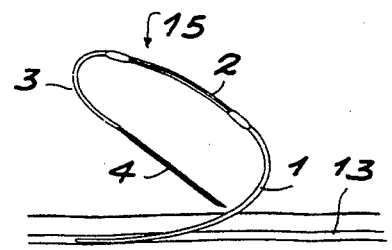
FIG. 17 is a diagram of the fourth stage of the tunnelling operation.
Figure 18:
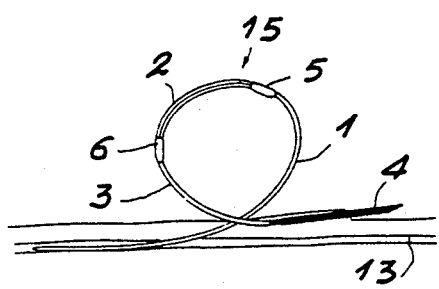
FIG. 18 is a diagram of the fifth stage of the tunnelling operation.
Figure 19:
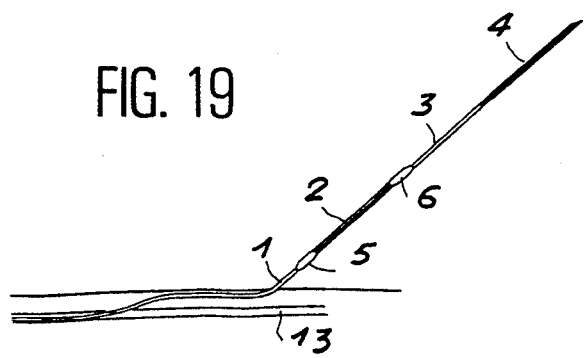
FIG. 19 is a diagram of the sixth stage of the tunnelling operation.
Figure 20:
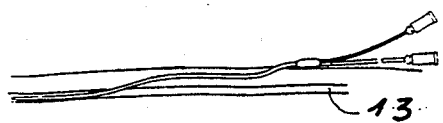
FIG. 20 is a diagram of the seventh stage of the tunnelling operation.

D—The practitioner then takes the tunnelling needle 4 and pricks exactly at the point of the initial puncture whilst slanting the catheter sideways (FIG. 17). To facilitate the remainder of the operation he can then make a slight cut with the lancet in order to enlarge the point where the catheter pipe and the tunnelling needle 4 cross.

E—The practitioner then advances the tunnelling needle 4 under the skin to the chosen point of emergence.

F—Next the practitioner continues to withdraw the tunnelling needle 4 slowly out of the skin. This needle then pulls out the pipe 3, followed by the connector 6 and the tubes 2a and 2b of the middle part 2, and finally the connector 5, the latter until the loop 15, formed when the tunnelling needle 4 was inserted, has completely disappeared (see FIG. 19).

G—At this stage of the operation, the practitioner can check that the catheter is positioned correctly by attaching, at the pointed end of the tunnelling needle 4, a special standardised female connector, preferably of polyurethane, by means of which he can check the reflux of blood or inject heparinated serum into the various conduits, those which are not used for the test being closed off by attaching a clamp provided for this purpose. Once this check has taken place and the last pipe 3 has in its turn been fitted with a closing clamp, the practitioner can cut the two tubes 2a and 2b in the desired order and fit them one at a time with a female connector 16, the end 17 of which is inserted into the corresponding tube.

The practitioner then checks the closure of the point of initial puncture and the closure of the point of emergence of the catheter with the usual dressings and can now proceed to make the required connections.

In this way, due to the distinctive design of the present catheter, it can be positioned by means of the tunnelling method, even if the catheter in question has several apertures. In the example described above, two apertures are provided in the distal part 1 of the catheter. However, this could comprise three apertures, or perhaps even more, in which case the middle part 2 would, for its part, comprise the same number of separate tubes, each connected to one of the apertures provided in the pipe of the distal part.

FIGS. 22 to 25 illustrate another embodiment of the catheter connectors according to the invention. This is designed in such a way that the catheter produces as little trauma as possible during tunnelling. To this end the external diameter of the body of each of the two connectors is equal to the total of the external diameters of the two tubes 2a and 2b of the middle part 2 of the catheter. Only the first connector 25, which joins the distal part 1 of the catheter to the middle part 2, is illustrated in the figures in question. However, the structure of the second connector is exactly the same.

To prevent any prior infiltration of liquid between the two tubes 2a and 2b of the middle part 2, and above all to avoid any difficulty when moulding on the body of the connector 25, the ends of these two tubes to be incorporated into the connector are first stuck together for a length of about 5 mm. In this embodiment the section of the connector is therefore reduced to the minimum since the walls of the two tubes 2a and 2b are flush with the sides, as can be seen from FIG. 24. In this case, the body of the connector 25 forms a sleeve only around the corresponding end of pipe 1.

It is, of course, advantageous to follow this with intimate welding of the pieces, as already described in the case of connector 5 in FIG. 2. To this end electrodes powered by a high-frequency current are used, and the same precautions as before are taken as regards the nature of the plastics used for the pieces to be joined.

Figure 22:
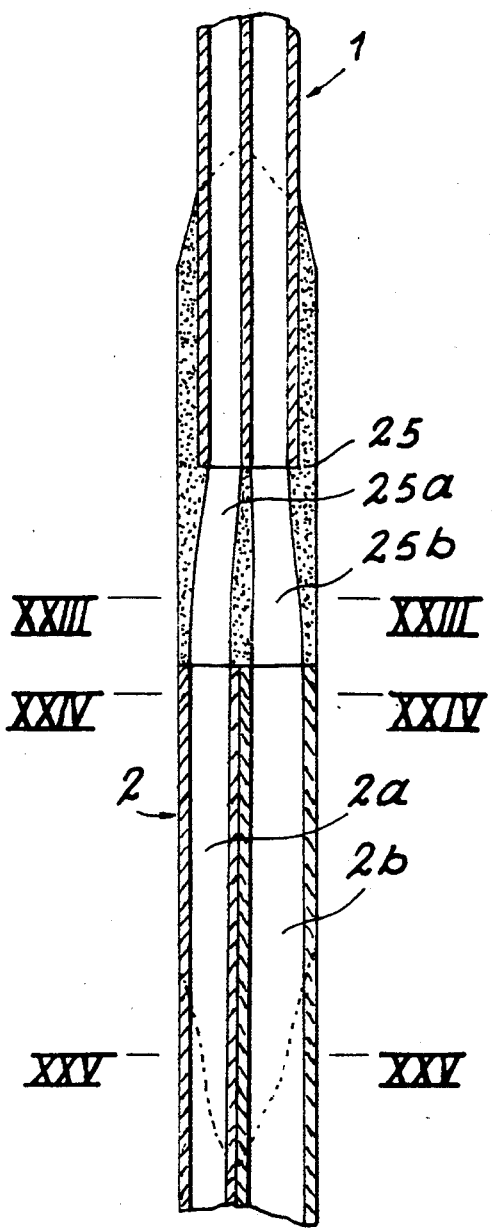
FIG. 22 is a view in longitudinal section of another embodiment of the connector illustrated in FIG. 2.
Figure 23:
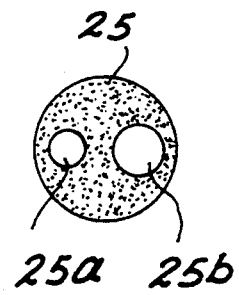
FIG. 23 is a view in transverse section along line XXIII—XXIII of FIG. 22.
Figure 24:
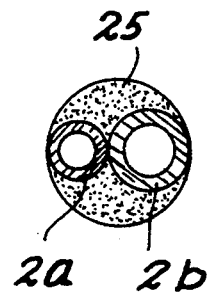
FIG. 24 is a view in transverse section along line XXIV—XXIV of FIG. 22.
Figure 25:
FIG. 25 is a view in transverse section along line XXV—XXV of FIG. 22.
Figure 26:
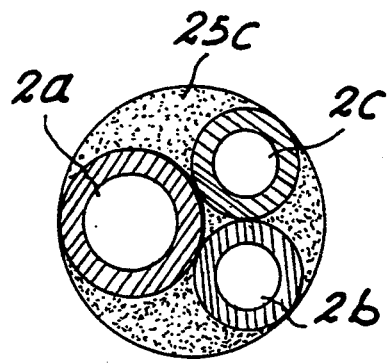
FIG. 26 is a view in transverse section of yet another embodiment of the connector in question, in the case of a catheter the distal part of which is made up of a pipe with three apertures.

FIG. 26 is a transverse section made at the same level as FIG. 24 (but on a different scale), in a variant 25c of the connector 25 from FIG. 22, this variant corresponding to the case in which the pipe 1 of the distal part of the catheter comprises three apertures. The middle part 2 of the catheter then comprises for its part three separate tubes 2a, 2b and 2c. In this case, the external wall of the connector 25a corresponds to a circle drawn around these three tubes after these tubes have been placed side by side so that the diameter of this circle is as small as possible. Consequently, even though in such a case the middle part 2 of the catheter comprises three separate tubes, the section of the connectors is still very small, which permits tunnelling of the catheter, as already described previously.

Finally it should be noted that the section of the connectors of the devices according to the invention may have a contour of a different shape from the circular form illustrated in the attached drawings, for example an elliptical or oval shape as close as possible to the external surface of the pipes, so as to reduce the total surface area of the section of these connectors.

I claim:

1. Intravascular catheter comprising a multi-aperture pipe intended for perfusion of medicines which are mutually incompatible in pure state and for carrying out several different functions, wherein, in order to permit implantation of said catheter by means of a "tunnelling" method, the multi-aperture pipe (1) forms only a distal part of said catheter, which also comprises:
    parallel side-by-side tubes (2a, 2b) that are separate from each other and are equal in number to the apertures of said multi-aperture pipe, and which extend back from said pipe to form a middle part (2) of said catheter capable of being passed under skin to carry out tunnelling,
    a single-aperture pipe (3) forming a proximal end of the catheter, which terminates in a rigid needle (4) suitable for carrying out tunnelling,
    two connectors (5 and 6) which serve respectively to join each aperture (1a, 1b) of the multi-aperture pipe (1) to one of the separate tubes (2a or 2b) of the middle part (2), and to connect opposite ends of these tubes (2a, 2b) to an adjacent end of the single-aperture pipe (3), each of these connectors being made up of a body made of plastic and moulded onto ends of the pipes (1, 3) and middle part (2) to be joined, each said connector having a tapered outer contour that provides a smooth transition between said connectors and said pipes and tubes.

2. Catheter as in claim 1, wherein an external wall of each connector (25, 25c) lies on with a circle drawn around the tubes (2a, 2b or 2a, 2b, 2c) of the middle part of the catheter.

3. Catheter comprising an intravascular multi-aperture pipe and a plurality of tubes that are separate from each other, said separate tubes being connected independently to apertures of said multi-aperture pipe, wherein said separate tubes are spaced apart from each other but are parallel to each other and are disposed side-by-side and said separate tubes are spaced longitudinally from said multi-aperture pipe at least by a predetermined space (E), a space between said separate tubes and said multi-aperture pipe being filled by a moulded material in such a manner that said pipes are intimately joined together and that said pipes are intimately joined to and connected with said multi-aperture pipe through independent channels formed inside said moulded material, said plurality of separate tubes being connected to a single aperture proximal pipe, each separate tube being spaced longitudinally from said single aperture proximal pipe by a space filled by a moulded material, each said moulded material having a tapered outer contour that provides a smooth transition between said moulded material and said pipes and tubes, said single aperture proximal pipe terminating in a rigid needle suitable for carrying out tunnelling.

* * * * *